(12) United States Patent
Li et al.

(10) Patent No.: US 7,744,914 B2
(45) Date of Patent: Jun. 29, 2010

(54) VASCULAR IMPLANT DEVICE

(75) Inventors: Song Li, Berkeley, CA (US); Rahul G. Thakar, Berkeley, CA (US)

(73) Assignee: Regents of the University of California, Oakland, CA (US)

( * ) Notice: Subject to any disclaimer, the term of this patent is extended or adjusted under 35 U.S.C. 154(b) by 1444 days.

(21) Appl. No.: 11/103,916

(22) Filed: Apr. 11, 2005

(65) Prior Publication Data

US 2006/0228389 A1    Oct. 12, 2006

(51) Int. Cl.
*A61F 2/00* (2006.01)
(52) U.S. Cl. .................................... 424/426
(58) Field of Classification Search ............... None
See application file for complete search history.

(56) References Cited

U.S. PATENT DOCUMENTS 5,645,740 A * 7/1997 Naiman et al. ......... 219/121.68

| | | | |
|---|---|---|---|
| 2004/0220660 A1* | 11/2004 | Shanley et al. | 623/1.16 |
| 2005/0209684 A1* | 9/2005 | Alexander et al. | 623/1.15 |
| 2006/0088571 A1* | 4/2006 | Chen et al. | 424/426 |
| 2007/0141100 A1* | 6/2007 | Sung et al. | 424/423 |

FOREIGN PATENT DOCUMENTS

WO        WO 03045582 A1 *    5/2003

OTHER PUBLICATIONS

Cordis Endovascular Product Information Sheet, 1999.*

* cited by examiner

*Primary Examiner*—Michael G Hartley
*Assistant Examiner*—Paul Dickinson
(74) *Attorney, Agent, or Firm*—Richard Aron Osman

(57) ABSTRACT

Vascular smooth muscle cells (VSMCs) adhere to and orient along micropatterned grooves having a depth of 1 to 10 μm and a width of 1 to 20 μm that are imposed on the surface of a vascular implant device. The VSMCs maintain an elongated morphology and reduced proliferation resulting in a decrease in occurrence of intimal hyperplasia upon device implantation.

18 Claims, No Drawings

VASCULAR IMPLANT DEVICE

FIELD OF THE INVENTION

The field of the invention is a micropatterned vascular implant for reducing proliferation of vascular smooth muscle cells.

BACKGROUND OF THE INVENTION

Micropatterned surfaces have been used for regulating growth, migration and differentiation of various cell types on a variety of materials, and using a variety of topographical dimensions (see e.g. Folch et al, 2000; Thapa et al, 2003; Palmaz et al., 1999; and Miller et al, 2003). Typically, these studies are designed to promote growth of adherent cells in defined geometry—to micropattern adherent cells—, and to control their morphology, migration or differentiation. For example, when the substrate poly(lactic-co-glycolic acid) (PLGA) is micropatterned with 10, 20, and 30 μm wide channels separated by cell adhesion resistant copolymers of poly (OEGMA-co-MA) or poly-OEGMA, cultured fibroblasts reportedly spread exclusively within the channels and adopt elongated shapes along the channels (Lin et al, 2005).

Similarly, vascular smooth muscle cells (VSMCs) cultured on a micropatterned surface of 20 μm wide ridges of Nafion separated by 80 μm wide troughs of a cell resistant copolymer reportedly achieve parallel, single-file, end-to-end growth (Salloum et al, 2005). Spatial control over endothelial cell spreading and orientation was reportedly achieved by culturing the cells on micropatterned chitosan films with grooves separated by plateau regions coated with a material that resists cell adhesion (Wang and Ho, 2004), and a microscopic pattern of parallel grooves on a metallic surface increases endothelial cell migration rates (Palmaz et al, 1999).

We have previously reported that micropatterned matrix proteins and topography control VSCM morphology and function, wherein cells cultured on a PLGA surface micropatterned with channels 30 μm wide and 25 μm deep achieved an elongated morphology and reduced proliferation (Thakar et al, 2003).

During restenosis VSMCs convert from a contractile phenotype to a proliferative phenotype and migrate to the lumen of the artery, resulting in intimal hyperplasia, which is a significant cause of morbidity in patients with engineered vascular grafts. Various materials, coatings, drug impregnations, and designs have been employed in vascular grafts and stents to combat this invasion of VSMCs into the lumen of the artery.

Here we report that we can dramatically reduce VSMC proliferation on vascular devices by fabricating on the device surface very narrow and shallow elongate microgrooves. The mechanism behind this inhibitory phenomenon is not yet understood, but the subject groove cross-sectional dimensions apparently do not permit complete entrenchment of the VSMC as with prior art micropatterning.

Other Relevant References

Aspects of this invention were disclosed at the Nov. 7-10, 2004 American Heart Association (AHA) conference (New Orleans, La.), and the Oct. 13-16, 2004 Biomedical Engineering Society (BMES) conference (Philadelphia, Pa.)

SUMMARY OF THE INVENTION

One aspect of the invention is a vascular implant device comprising a surface micropatterned with parallel grooves to which vascular smooth muscle cells (VSMCs) adhere to and orient along, wherein the grooves have a depth of 1 to 10 μm, and a width of 1 to 20 or 30 μm, and the micropattern reduces proliferation of the VSMCs. In particular embodiments, the implant device is a vascular graft or stent.

In a preferred embodiment, the grooves have a depth of 2 to 5 μm, and a width of 5-10 μm.

In one embodiment, the surface comprises a polymeric material selected from the group consisting of poly-(D,L-lactide-co-glycolide) (PLGA), poly-(dimethylsiloxane) (PDMS), poly-(L-lactide-co-caprolactone-co-glycolide) (PLCG), polycaprolactone (PCL), polylactic acid (PLA), polystyrene, polyurethane, ePTFE, and Dacron.

In another embodiment, the surface comprises a metallic material selected from the group consisting of stainless steel, a nickel-titanium alloy, and a cobalt chromium alloy.

Another aspect of the invention is a method of reducing proliferation of VSMCs on a vascular implant device comprising a surface, the method comprising the steps of: (a) implanting the device in vascular tissue of a recipient wherein imposed on the surface of the device is a micropattern of parallel grooves, wherein the grooves have a depth of 1 to 10 μm, and a width of 1 to 20 μm, wherein the VSMCs adhere to and orient along the grooves, and the micropattern reduces proliferation of the VSMCs; and (b) detecting on the surface of the device a resultant reduced proliferation of the VSMCs. In particular embodiments, the implant device is a vascular graft or stent.

In one embodiment of the method of the invention, the surface comprises a polymeric material selected from the group consisting of PLGA, PDMS, PLCG, PCL, PLA, polystyrene, polyurethane, ePTFE, and Dacron.

In another embodiment of the method of the invention, the surface comprises a metallic material selected from the group consisting of stainless steel, a nickel-titanium alloy, and a cobalt chromium alloy.

In a preferred embodiment of the method of the invention, the grooves have a depth of 2 to 5 μm, and a width of 5-10 μm.

DETAILED DESCRIPTION OF PARTICULAR EMBODIMENTS OF THE INVENTION

The invention is an implant device comprising a surface with a micropattern of parallel grooves having a depth of 1 to 10 μm and a width of 1 to 20 or 30 μm. When smooth muscle cells (SMCs) are contacted with the device, they adhere to and orient lengthwise along the grooves and exhibit reduced proliferation. The implant device can be any type of biomedical device that is implanted into a tissue or an organ where it is desired to have SMCs adhere to the device and maintain an elongated phenotype and reduced proliferation. In particular embodiments the implant device is a vascular stent or graft that is contacted with vascular smooth muscle cells (VSMCs); these particular embodiments are detailed herein. However, the invention is also applicable to other types of implant devices such as ureteral grafts and stents and ventricular grafts (see e.g. Matsubayashi et al, 2003).

A micropattern is imposed on the surface of the implant device, and comprises a plurality of parallel, elongate grooves separated by plateau regions. The grooves are positioned such that when the device is implanted into a recipient, the grooves are aligned to conform to the desired direction of VSMC alignment. For example, on vascular stents and grafts, the grooves are preferably oriented circumferentially around the device, to promote circumferential alignment of the VSMCs. The length of the grooves is determined by the intended use of the implant device, and is usually at least 1000, 500, 200 or 100 μm, and the width of the grooves is 1 to 30 μm, and is preferably 1-20 or 1-15 µm, and more preferably 1-10 µm wide. The depth of the grooves is 1 to 10 µm, preferably 1 to 5 µm, and more preferably 1 to 3 µm. The grooves are preferably spaced between about 1 and 30 µm apart, and preferably 1-20 or 1-15 µm, and more preferably 1-10 µm. In particular embodiments, the grooves have a depth of 2 to 5 µm, and a width of 5 to 10 µm, and are spaced by plateau regions about equal to the groove width. We find VSMC proliferation inhibition using a wide variety of groove cross-sectional geometries within these dimensions, including square and rectangular, semi-circular and semi-oval, and v-shaped cross-sections, wherein the recited maximum dimensions within the cross-sections.

In one embodiment, the implant device is a vascular graft. Vascular grafts are typically fabricated from biocompatible polymeric materials. Numerous suitable polymeric materials are widely available such as poly-(dimethylsiloxane) (PDMS), polystyrene, polyurethane, expanded polytetrafluoroethylene (ePTFE), and Dacron. In certain embodiments, the polymeric material is biodegradable such as poly-(D,L-lactide-co-glycolide) (PLGA), poly-(L-lactide-co-caprolactone-co-glycolide) (PLCG), polycaprolactone (PCL), and polylactic acid (PLA).

Methods for imposing or microfabricating a micropattern on the surface of a polymeric vascular graft material are known in the art such as photolithography (see e.g. Revzin et al, 2001), microcontact printing (see e.g. Lin et al, 2005) and soft lithography (see e.g. Xia and Whitesides, 1998). In an exemplary method described by Thakar et al (2003), a silicon mold is microfabricated by coating a silicon wafer with a negative photoresist and exposing it to UV light through a photomask having the desired groove width and length. The photoresist without UV polymerization is developed away, leaving a patterned surface. Then, the silicon wafer is etched by using an ion etcher to form the grooves and the remaining photoresist is washed away. A polymer solution is poured into the silicon mold and allowed to evaporate forming a polymer film.

The device may be fabricated so as to have differing surface chemistries at the grooves and the plateau regions. For example, the grooves may be optionally coated with a composition to further promote SMC adhesion and differentiation (e.g. extracellular matrix components such as fibronectin, collagen and proteoglycans), and/or the plateau may be coated with a molecule or composition to resist cell adhesion, such as Poly(oligoethyleneglycol methacrylate) (poly-OEGMA) or poly(oligoethyleneglycol methacrylate-co-methacrylic acid) (poly(OEGMA-co-MA)). In particular embodiments, the device is constructed and used without any cell adhesion resistant material between the grooves. For simplicity and ease of fabrication, in a preferred embodiment the groove and plateau regions of the device have the same surface chemistry absent any cell adhesion or cell adhesion resistant material.

Prior to implantation, the surface of the vascular graft may be seeded with muscle cells using known methods (see e.g. Yu et al, 2003). The cells are allowed to adhere to the grooves and the device is implanted into a recipient. In certain embodiments, the graft may be seeded with endothelial cells. For example, the graft may be fabricated to form a vessel having a luminal surface that is seeded with endothelial cells, and an outer surface that is micropatterned with the grooves aligned circumferentially around the vessel. The endothelialized graft may be implanted into a recipient where endogenous SMCs adhere to the grooves. Alternatively, the endothelialized graft may also be seeded with SMCs that adhere to the grooves prior to implantation. In a further embodiment, the graft may be seeded with SMCs that adhere to the grooves, and may be additionally seeded with endothelial cells such that the resulting graft comprises an intimal layer of endothelial cells and a medial layer of SMCs.

Vascular stents are commonly fabricated from metallic materials such as stainless steel, nickel-titanium alloys (e.g. nitinol), cobalt chromium alloys, etc. Suitable stents materials are commercially available from a large number of manufacturers including Johnson & Johnson, Abbot Laboratories, Boston Scientific, Guidant, Conor Medicals, Arterial Vascular Engineering, Inc., etc., and include drug-eluting stents. Methods for imposing or microfabricating a micropattern on the surface of a metallic stent material are known in the art; see, e.g. Palmaz et al, J Vasc Interv Radiol (1999) 10:439-44; Park et al, Biotechnol. Prog. 2003, 19, 243-253; etc. Additional suitable technologies for generating the subject micropatterns on metallic stent surfaces include microlaser techniques e.g pulsed Nd:YAG laser machining (see, e.g. Raju et al., J Miss State Med Assoc. 2004 October; 45(10):290-7; Bereznai et al., Biomaterials 24, 2003, 4197-4203; Berry et al., Proc Instn Mech Engrs Vol 216 Part H: J Engineering in Medicine, p. 211-14; Wu et al., Lasers in Surgery and Medicine 31:333-338, 2002; Kruger et al., Adv Polym Sci, 2004, 168:247-289), Ti—O/Ti—N complex film coating prepared with plasma immersion ion implantation and deposition (e.g. Huang et al., 14th Intnl Conf on Ion Beam Modification of Materials, Monterey, Calif., Sep. 5-10, 2004), and wet stamping (e.g. Campbell et al., Langmuir. 2005 Mar. 29; 21(7): 2637-40), etc. Alternatively, metallic stent surfaces may be covered with an elastomeric film such as segmented polyurethane (SPU) which is micropatterned, e.g. using a KrF excimer laser (see e.g. Nakayama 2002). Vascular stents may be advantageously patterned on the interior luminal surface, the exterior surface, or both.

The micropattern reduces VSMC proliferation relative to the same surface material lacking the micropattern. A resultant reduced proliferation of the VSMCs can be detected by comparing VSMC proliferation endpoints or proliferation rates on micropatterned and unpatterned surfaces, for example with a BrdU cell proliferation assay. For devices that have been implanted into a recipient, reduced proliferation can be detected in post surgery follow-up by routine imaging (e.g. intravascular ultrasound, magnetic resonance angiography, arteriography, CT angiography, angioscopy, etc.). In particular embodiments, the proliferation is reduced at least 20, 50, 80, or 90%.

Another aspect of the invention is a method of reducing VSMC proliferation on a vascular implant device. The method comprises implanting the device in vascular tissue of a recipient. Imposed on the surface of the device is a micropattern of parallel grooves, wherein the grooves have a depth of 1 to 10 µm and a width of 1 to 20 µm. The VSMCs adhere to and orient along the grooves, and the micropattern reduces proliferation of the VSMCs. The recipient can be any mammal in need of vascular stent or graft therapy. In one embodiment, the recipient is an animal model of restenosis and vascular disease (e.g. mouse, rabbit, pig, etc.). In a preferred embodiment the recipient is human.

Example I

SMCs Seeded on Micropatterned PLGA Exhibit Elongated Morphology and Reduced Proliferation A silicon wafer is used to generate a template for a poly (dimethylsiloxane) (PDMS) mold. A mask with patterned emulsion strips 10 µm wide, 100 µm apart, and 1-cm in length is generated. To transfer the pattern to the silicon wafer, the wafer is spin-coated with a photoresist (OIR 897-10I, Arch Chemicals, Norwalk, Conn.), and a mask aligner is used to expose the wafer to ultraviolet light through the emulsion mask with pre-printed pattern. The unexposed photoresist is washed away during the development process, leaving behind a microfabricated template. Then, the silicon wafer is etched using an STS Deep Reactive Ion Etcher to form 2.5 µm deep channels and the remaining photoresist is washed away.

PLGA (50:50) (Polysciences, Warrington, Pa.) is dissolved in chloroform and agitated on a shaker for 24 h. The solution is filtered through 0.45 µm pores before use. The solution is poured onto the silicon mold and the solvent is allowed to evaporate, forming thin PLGA films. The films are detached from the silicon mold and sterilized in 70% ethanol for 30 min.

Bovine aortic SMCs (BSMCs) are isolated by scraping the luminal surface of bovine aortas with a surgical knife to denude the endothelial cells. Small pieces of the underlying tissue (1 mm thick) are removed for culture to allow the emigration of SMCs. Cell purity is confirmed by immunofluorescent staining of SMC markers α-actin and calponin. The cells are cultured in a complete medium consisting of Dulbecco's modified Eagle's medium, 10% fetal bovine serum, and 1 mM penicillin-streptomycin, all obtained from Gibco-BRL (Grand Island, N.Y.). Cell cultures are maintained in a humidified 95% air-5% $CO_2$ incubator at 37° C. All experiments use cultures prior to passage 10.

The PLGA films are coated with 0.8 mg/ml of type I collagen and BSMCs are seeded on the PLGA films and cultured for 24 h to allow the cells to adhere to the surface. To detect BSMC proliferation, the cells are incubated with 10 µM 5-bromo-2'-deoxyuridine (BrdU) (Sigma Aldrich, St. Louis, Mo.) for 2 h. Then, samples are fixed with 4% paraformaldehyde and permeabilized with 0.5% Triton X-100. BrdU is stained by a mouse anti-BrdU antibody (PharMingen, San Diego, Calif.) and an FITC-anti-mouse antibody. The cell nuclei are stained with 10 µM Hoechst (Sigma) for 5 min. The percentage of SMCs that incorporate BrdU correlates with the proliferation rate of SMCs. SMCs grown on micropatterned PLGA have a significantly lower proliferation rate than cells grown on unpatterned PLGA.

Effects of micropatterning on cell adhesion and morphology is observed on BSMCs cultured for 24 h on micropatterned or unpatterned control surfaces. After fixation and permeabilization, the cells are stained with mouse anti-N-cadherin and FITC-conjugated anti-mouse antibodies, followed by rhodamine-phalloidin staining on F-actin, and the cells are visualized by confocal microscopy. Phalloidin staining reveals that cells on the control surface exhibit random and unorganized cell-cell adhesion and have prominent actin stress fibers, while the cells grown in the grooves have a more elongated morphology, less actin filaments, and less N-cadherin staining. In the cells grown in grooves, N-cadherin locates at the two ends of the cells and tends to align in the direction of the actin fibers.

Example 2

Micropatterned PLGA Graft Seeded with Smooth Muscle and Endothelial Cells and Reduction of Intimal Hyperplasia in a Rabbit Model This animal study is adapted from published methods (Yu et al, 2003). Endothelial cells (EC) and smooth muscle cells (SMCs) are isolated from the jugular vein of a rabbit. New Zealand White rabbits weighing approximately 4 kg are anesthetized with intramuscular injection of ketamine (40 mg/kg) and xylazine (10 mg/kg). The jugular vein is exposed, ligated, excised, placed in transport solution, and transported from the operating room to the laboratory in RPMI 1640 medium (Gibco BRL, Gaithersburg, Md.) containing 20 mmol/L of HEPES (N-2-hydroxyethylpiperazine-N-2-ethanesulfonic acid), 2 mmol/L of L-glutamine, 50 U/mL of penicillin, 50 µg/mL of streptomycin, 2.5 µg/mL of gentamicin, and 2.5 µg/mL of amphotericin B. The veins are flushed with RPMI medium, clamped at one end, filled with 0.1% collagenase I (Gibco BRL) in Dulbecco phosphate-buffered saline solution (DPBS), and incubated for 10 minutes at 37° C. The dissociated ECs are pelleted with centrifugation at room temperature, at 1200 rpm (200 g) for 5 minutes. Cells are resuspended and plated onto 0.1% fibronectin precoated dishes with EC medium containing MCDB 131 medium (Gibco BRL), 20% fetal bovine serum (FBS) (Hyclone, Logan, Utah), 50 µg/mL of porcine intestinal mucosa-derived heparin (Sigma, St Louis, Mo.), 50 µg/mL of EC growth supplement (Becton Dickinson, Franklin Lakes, N.J.), 2 mmol/L of L-glutamine (Gibco BRL), and the antibiotics (penicillin, streptomycin, gentamicin, amphotericin B).

After EC dissociation, the SMCs are harvested as follows. The vein is incised longitudinally, and the intimal layer is scraped off with a scalpel. The opened vein is incubated with DPBS containing collagenase I (1.8 mg/mL), and elastase (0.2 mg/mL), for 1 hour at 37° C. The single-cell suspension supernatant is removed and pelleted with centrifugation at 1200 rpm for 5 minutes. The SMCs are resuspended and cultured in Williams medium (Gibco BRL) containing 20% FBS, L-glutamine (2 mmol/L), and the same antibiotics. ECs are characterized by cellular architecture under phase contrast microscopy, and by fluorescent staining for von Willebrand factor and low-density lipoprotein uptake. SMCs are identified by the presence of cytoplasmic smooth muscle α-actin. All cells are maintained in a humidified 37° C. incubator with 5% carbon dioxide, and are passaged at a 1:5 ratio and used for experiments between passages 2 through 10.

PLGA grafts are fabricated to have a surface micropattern of parallel grooves (10 µm wide×2.8 µm deep). The surface is coated with fibronectin (0.1 mg/mL in PBS; Gibco BRL). SMCs are seeded on the grafts and cultured for 1 day before ECs are seeded over SMC.

New Zealand white rabbits are anesthetized and endotracheal tubes are inserted. The infrarenal aorta is controlled with a curved bulldog clamp, and a longitudinal aortotomy is made with an 11-blade scalpel. The incision is lengthened to 4 mm. A 5-cm-long, 4-mm-diameter PLGA graft seeded with autologous cells is then sewn in end-to-side with running 6-0 Prolene suture. Once the proximal anastomosis is complete, the distal anastomosis are similarly constructed just above the aortic bifurcation. After graft placement, the aorta proximal to the distal anastomosis is ligated, converting the anastomosis to a functional end-to-end anastomosis. Buprenorphine (0.05 mg/kg intramuscularly) is administered for postoperative analgesia at 12-hour intervals for 4 days. At graft harvest after 30-day, or 100-day implantation, heparin (400 IU per rabbit) is injected intravenously to prevent fresh clot formation.

The recovered grafts after 30-day or 100-day implantation are flushed with PBS and cut into two parts: one part (a third of the graft) is opened longitudinally for luminal analysis for thrombosis; the other part (two thirds of the graft) is further cut into three segments: proximal anastomosis (A), proximal third of graft (P), and middle segment of graft (M). The segments are embedded in ornithine carbamoyltransferase and frozen in liquid nitrogen. Cut sections (4 µm thick) are mounted on glass slides and stained with hematoxylineosin. The thickness of the neointima is measured with a microscopic ruler at 8 evenly distributed locations on the graft circumference.

Example 3

Effect of Micropatterned Stent in a Porcine Coronary Restenosis Model

The animal study is adapted from published methods (Kim et al, 2005) and conforms to the guidelines of the American Heart Association on animal research. Juvenile farm pigs (25-30 kg body weight) are given oral acetylsalicylic acid (100 mg/day) and ticlopidine (250 mg/day) one day preoperatively and then daily thereafter until death. The animals are anesthetized with ketamine (12 mg/kg im) and xylazine (8 mg/kg im) and additional midazolam is injected intravenously during the procedure. Using sterile surgical technique, the left carotid artery is cannulated with an 8Fr hemostatic sheath through a midline cervical incision. Heparin (250 IU/kg) is administered through the arterial sheath and baseline coronary angiography is performed using guiding catheters. The segment of coronary artery to be stented is selected to allow more than 1.2-fold oversizing by visual estimation. The nitinol stents are 3.0×15 mm and are unpatterned (control) or are etched using diamond particles to form a micropattern of parallel grooves, 10 μm wide and 2.8 μm deep, imposed circumferentially on the surface of the stent. The stent is placed using an inflation pressure of 8-12 atmosphere for 20-30 s. After intracoronary administration of 200 μg nitroglycerin, angiography is repeated to confirm adequate stent expansion and vessel patency. The carotid arteriotomy site is ligated and the neck wound closed. Follow-up angiography is performed 28 days after stent implantation and then the animals are euthanized.

After euthanasia, the stented coronary arterial segments are carefully dissected with 1 cm of the vessel both proximal and distal to the stent and then fixed in a 10% formalin solution. Specimens are paraffin-embedded, sectioned, and stained with hematoxylin-eosin. All sections are examined with a light microscope. Morphometric analysis is performed using a computerized morphometry program (Visus 2000 Visual Image Analysis System). A minimum of 3 sections for each segment is analyzed and the results are averaged. The lumen, neointima, and total vessel cross-sectional areas are measured and recorded. The areas of external elastic lamina (EEL), internal elastic lamina (IEL), and lumen are measured by digital planimetry to obtain the neointimal area (IEL area—lumen area). Morphometric area of stenosis is calculated as 100 (1—lumen area/IEL area). The extent of arterial injury, inflammation, and re-endothelialization is assessed.

The stent filaments are removed without distorting or damaging the artery. The sections are treated with 1:100 diluted mouse anti-proliferating cell nuclear antigen (PCNA) antibody (clone PC 10, DAKO) to study SMC proliferation in the neointima. The samples are incubated, developed, and counterstained with hematoxylin. The SMC density of 5 randomly chosen areas (0.1 mm$^2$) of the neointima is measured with computer assistance at 400 magnification. The percentage of proliferating SMCs is obtained by dividing the number of PCNA-positive SMCs by the total number of SMCs in each field and the results are averaged. In addition, a modification of Movat's pentachrome stain using a saffron/Alcian blue combination is applied to evaluate the extracellular matrix of the neointima. A reduction in neointimal area in the micropatterned stents as compared to control stents indicates that the micropatterned stents effectively inhibit SMC proliferation.

Example 4

Clinical Application

Clinical applications are modeled after the West European Stent Trial (WEST) (Emanuelsson et al, 1998) to assess the safety and efficacy of nitinol stents micropatterned with parallel grooves (10 μm wide×2.8 μm deep) imposed circumferentially on the surface of the stent. Patients with angina pectoris to be treated with the stent are recruited. Following stent implantation, patients are given heparin infusion and oral coumadin treatment is maintained for 3 months. Quantitative angiography is performed to measure decreases in minimum lumen diameter after stent deployment at 6 months. The in-stent restenosis rate is determined and any appearances of a stenosis in the target vessel outside the stent are noted. Patients are monitored for intimal hyperplasia, bleedings, and vascular complications and incidence of major adverse cardiac events during 12 months follow-up. This study demonstrates the degree of safety and efficacy of the micropatterned stent and lower incidence of intimal hyperplasia resulting from SMC proliferation relative to data from unpatterned stents.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Chen et al, Proc Natl Acad Sci USA. (2003) 100:1499-504
Emanuelsson et al, J Invasive Cardiol. (1998) April; 10 Suppl B: 12B-19B
Folch et al, J Biomed Mater Res. (2000) 52:346-53
Kim et al, Circ J. (2005) 69(1):101-6.
Lin et al, Biomaterials (2005) 26:3655-3662
Matsubayashi et al, Circulation. (2003) 108 Suppl 1:II219-25.
Miller et al, Biomaterials (2004) 25:53-61.
Nakayama et al, (2002) J Biomed Mater Res A. (2003) 64:52-61.
Revzin et al, Langmuir (2001) 17:5440-7
Salloum et al, Biomacromolecules (2005) 6:161-167)
Thakar et al, BBRC (2003) 307:883-90
Thapa et al, Biomaterials (2003) 24:2915-26.
Yu et al, J Vasc Surg. (2003) 38:557-63.
Xia and Whitesides, Annu. Rev. Mater. Sci. (1998) 28:153-84

What is claimed:

1. A vascular graft comprising a surface with a micropattern of parallel grooves and plateau regions, wherein vascular smooth muscle cells (VSMCs) can adhere and orient along said grooves, wherein the grooves have a depth of 1 to 10 μm, and a width of 1 to 20 μm, and the micropattern reduces proliferation of the VSMCs, wherein the graft is fabricated from a polymeric material selected from the group consisting of poly-(D,L-lactide-co-glycolide) (PLGA), poly-(dimethylsiloxane) (PDMS), poly-(L-lactide-co-caprolactone-co-glycolide) (PLCG), polycaprolactone (PCL), polylactic acid (PLA), polystyrene, polyurethane, ePTFE, and polyethylene terephthalate.

2. The vascular graft of claim 1, wherein polymeric material is poly-(D,L-lactide-co-glycolide) (PLGA).

3. The vascular graft of claim 1, fabricated so as to have differing surface chemistries at the grooves and the plateau regions.

4. The vascular graft of claim 1, fabricated so as to have differing surface chemistries at the grooves and the plateau regions, wherein the grooves are coated with a composition that further promotes smooth muscle cell adhesion and differentiation, wherein the composition is an extracellular matrix component selected from the group consisting of fibronectin, collagen and proteoglycans.

5. The vascular graft of claim 1, fabricated so as to have differing surface chemistries at the grooves and the plateau regions, wherein the plateau regions are coated with a composition that resists cell adhesion and is selected from the group consisting of poly(oligoethyleneglycol methacrylate) (poly-OEGMA) and poly(oligoethyleneglycol methacrylate-co-methacrylic acid) (poly(OEGMA-co-MA)).

6. The vascular graft of claim 1, fabricated so as to have differing surface chemistries at the grooves and the plateau regions, wherein the grooves are coated with a composition that further promotes smooth muscle cell adhesion and differentiation, wherein the composition is an extracellular matrix component selected from the group consisting of fibronectin, collagen and proteoglycans, and the plateau regions are coated with a composition that resists cell adhesion and is selected from the group consisting of poly(oligoethyleneglycol methacrylate) (poly-OEGMA) and poly(oligoethyleneglycol methacrylate-co-methacrylic acid) (poly(OEGMA-co-MA).

7. The vascular graft of claim 1, wherein the vascular graft is constructed and used without any cell adhesion resistant material between the grooves.

8. The vascular graft of claim 1, wherein the groove and plateau regions of the vascular graft have the same surface chemistry and are absent any cell adhesion or cell adhesion resistant material.

9. The vascular graft of claim 1, wherein the surface is seeded with muscle cells and the muscle cells are adhered to the grooves prior to implantation of the device vascular graft.

10. The vascular graft of claim 1, wherein the graft is fabricated to form a vessel having a luminal surface that is seeded with endothelial cells, and an outer surface that is micropatterned with the grooves, which are aligned circumferentially around the vessel.

11. The vascular graft of claim 1, wherein the graft is fabricated to form a vessel having a luminal surface that is seeded with endothelial cells, and an outer surface that is micropatterned with the grooves aligned circumferentially around the vessel, and the outer surface is seeded with smooth muscle cells that adhere to the grooves.

12. The vascular graft of claim 1, wherein the graft is seeded with smooth muscle cells that adhere to the grooves, and is additionally seeded with endothelial cells such that the graft comprises an intimal layer of the endothelial cells and a medial layer of the smooth muscle cells.

13. A method of making the vascular graft of claim 1, comprising the step of:
(a) imposing on the surface of a vascular graft a micropattern of parallel grooves to which grooves vascular smooth muscle cells (VSMCs) adhere and orient along, wherein the grooves have a depth of 1 to 10 µm, and a width of 1 to 20 µm, and the micropattern reduces proliferation of the VSMCs.

14. The method of claim 13, wherein the vascular graft is fabricated so as to have differing surface chemistries at the grooves and the plateau regions, wherein the grooves are coated with a composition that further promotes smooth muscle cell adhesion and differentiation, wherein the composition is an extracellular matrix component selected from the group consisting of fibronectin, collagen and proteoglycans, and the plateau regions are coated with a composition that resists cell adhesion and is selected from the group consisting of poly(oligoethyleneglycol methacrylate) (poly-OEGMA) and poly(oligoethyleneglycol methacrylate-co-methacrylic acid) (poly(OEGMA-co-MA).

15. A method of using the graft of claim 1, comprising the steps of:
implanting the vascular graft in vascular tissue of a recipient wherein the VSMCs adhere to and orient along the grooves, and the micropattern reduces proliferation of the VSMCs.

16. A method of using the vascular graft of claim 6, comprising the steps of:
(a) implanting the vascular graft in vascular tissue of a recipient wherein the VSMCs adhere to and orient along the grooves, and the micropattern reduces proliferation of the VSMCs.

17. The vascular graft of claim 1, further comprising the VSMC's adhered to and oriented along the grooves, thereby having reduced proliferation.

18. The vascular graft of claim 1, wherein the grooves have a depth of 2 to 5 µm, and a width of 5-10 µm.

* * * * *